(12) United States Patent
Takino

(10) Patent No.: US 9,375,360 B2
(45) Date of Patent: Jun. 28, 2016

(54) DISPOSABLE DIAPER

(75) Inventor: Shunsuke Takino, Kagawa (JP)

(73) Assignee: Unicharm Corporation, Ehime (JP)

( * ) Notice: Subject to any disclaimer, the term of this patent is extended or adjusted under 35 U.S.C. 154(b) by 196 days.

(21) Appl. No.: 13/978,210

(22) PCT Filed: Jan. 5, 2012

(86) PCT No.: PCT/JP2012/050111
§ 371 (c)(1),
(2), (4) Date: Jul. 3, 2013

(87) PCT Pub. No.: WO2012/093699
PCT Pub. Date: Jul. 12, 2012

(65) Prior Publication Data
US 2013/0289513 A1    Oct. 31, 2013

(30) Foreign Application Priority Data

Jan. 7, 2011    (JP) ................ 2011-002161

(51) Int. Cl.
*A61F 13/15* (2006.01)
*A61F 13/49* (2006.01)
*A61F 13/496* (2006.01)

(52) U.S. Cl.
CPC ....... *A61F 13/49009* (2013.01); *A61F 13/4902* (2013.01); *A61F 13/496* (2013.01); *A61F 13/49017* (2013.01); *A61F 2013/49022* (2013.01); *A61F 2013/49095* (2013.01)

(58) Field of Classification Search
CPC .............. A61F 13/49009; A61F 13/49017; A61F 13/4902; A61F 13/496; A61F 2013/49022; A61F 2013/49095
See application file for complete search history.

(56) References Cited

U.S. PATENT DOCUMENTS

| 6,436,083 B1 | 8/2002 | Mishima et al. |
| 6,685,688 B2* | 2/2004 | Mishima et al. ......... 604/385.22 |
| 2005/0107764 A1 | 5/2005 | Matsuda et al. |
| 2006/0157188 A1* | 7/2006 | Thorson et al. ............... 156/164 |

(Continued)

FOREIGN PATENT DOCUMENTS

| JP | 2001-8968 A | 1/2001 |
| JP | 2002-209938 A | 7/2002 |
| JP | 2005-160686 A | 6/2005 |
| JP | 2005-287699 A | 10/2005 |

(Continued)

OTHER PUBLICATIONS

International Search Report based on corresponding PCT application No. PCT/JP2012/050111 dated Apr. 3, 2012 (4 pgs).

*Primary Examiner* — Bradley Philips
(74) *Attorney, Agent, or Firm* — Brinks Gilson & Lione

(57) ABSTRACT

To facilitate a continuous tight fit of a diaper to a wearer, a disposable diaper having one waist opening and a pair of leg openings is provided with: a front-side section; a back-side section; a crotch section; and a pair of extensible or stretchable leg sheets. Longitudinal peripheral edge regions and inner lateral edge regions of the leg sheets are respectively joined, on one side of the crotch section, to lower edge regions of the front-side section and back-side section and lateral edge regions of the crotch section. The leg sheets each have notches facing inward from the outer lateral edges thereof. The pair of leg openings are defined by joining outer lateral edge regions of the leg sheets adjacent to front-side starting ends of the notches, and outer lateral edge regions of the leg sheets adjacent to back-side starting ends of the notches.

10 Claims, 18 Drawing Sheets

(56) References Cited

U.S. PATENT DOCUMENTS

| | | | |
|---|---|---|---|
| 2008/0140042 A1* | 6/2008 | Mukai et al. | 604/385.23 |
| 2010/0154970 A1 | 6/2010 | Lohoff | |
| 2011/0022020 A1 | 1/2011 | Wakasugi et al. | |
| 2011/0118692 A1 | 5/2011 | Sakaguchi | |
| 2013/0281958 A1* | 10/2013 | Back et al. | 604/385.25 |

FOREIGN PATENT DOCUMENTS

| | | |
|---|---|---|
| JP | 2008-80026 A | 4/2008 |
| JP | 2009-207844 A | 9/2009 |
| JP | 2010-279712 A | 12/2010 |
| WO | WO 2008/066006 A1 | 6/2008 |

* cited by examiner

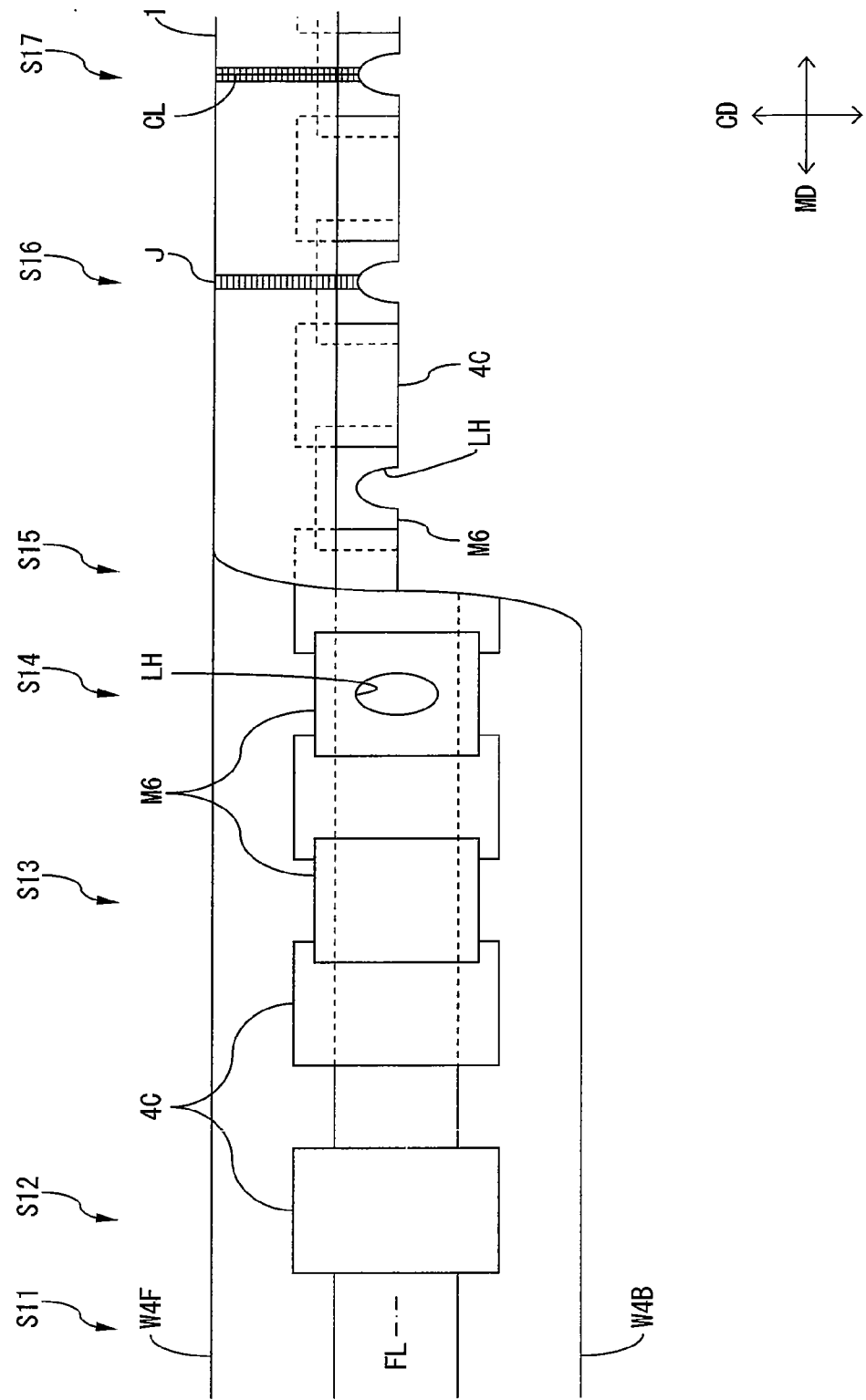

DISPOSABLE DIAPER

RELATED APPLICATION

This application is a 35 U.S.C. §371 national phase filing of International Patent Application No. PCT/JP2012/050111, filed Jan. 5, 2012, through which and to which priority is claimed under 35 U.S.C. §119 to Japanese Patent Application No. 2011-002161, filed Jan. 7, 2011.

TECHNICAL FIELD

The present invention relates to a disposable diaper.

BACKGROUND ART

Known in the art is a disposable diaper which is provided with a single torso opening and a pair of leg openings, which disposable diaper is provided with a front part and back part which are separated from each other in the length direction when the diaper is spread open and with an elastic sheet which is joined with these front part and back part, the side edge regions of the front part and back part being joined by tape fasteners (see PLT 1). If doing this, the elastic sheet contacts the wearer, so the diaper easily follows movement of the wearer and slippage of the diaper downward can be suppressed.

CITED REFERENCE LIST

Patent Literature

PLT 1: Japanese Patent Publication No. 2001-8968A

SUMMARY OF INVENTION

Technical Problem

However, in the above-mentioned diaper, the tape fasteners are at positions separated from the elastic sheet, so the part of the elastic sheet which adjoins the front part and the part of the elastic sheet which adjoins the back part are not joined with each other. As a result, movement of the wearer causes the leg openings to expand larger and the elastic sheet is liable to separate from the wearer. Therefore, slippage of the diaper downward is liable to be unable to be sufficiently suppressed. Further, since the part of the elastic sheet which adjoins the front part and the part of the elastic sheet which adjoins the back part are not joined with each other, the elastic sheet parts are liable to separate from the front part and back part.

Solution to Problem

According to a first aspect of the present invention, there is provided a disposable diaper which is provided with a single torso opening and a pair of leg openings, wherein the disposable diaper is provided with a front part and back part and with a crotch part, the front part and back part are separated from each other in the length direction when the diaper is spread open, the crotch part extends in the length direction at an intermediate position in the traverse direction, the diaper is further provided with a pair of leg sheets which have stretchability or elasticity, length direction circumferential edge regions and an inward side edge region of one leg sheet are respectively joined at one side of the crotch part with the bottom edge region of the front part and the bottom edge region of the back part and with the side edge region of the crotch part, whereby that one leg sheet is arranged at one side of the crotch part at the space between the front part and back part, length direction circumferential edge regions and an inward side edge region of the other leg sheet are respectively joined at the other side of the crotch part with the bottom edge region of the front part and the bottom edge region of the back part and with the side edge region of the crotch part, whereby that other leg sheet is arranged at the other side of the crotch part at the space between the front part and back part, the diaper has depressed parts which extend from the two side edges inward when spread open, and leg sheets which adjoin front-side starting ends of depressed parts or the front part and leg sheets which adjoin back-side starting ends of depressed parts or the back part are joined with each other, whereby a pair of leg openings are defined.

According to a second aspect of the present invention, there is provided a disposable diaper which is provided with a single torso opening and a pair of leg openings, wherein the disposable diaper is provided with a front part and back part, the front part and back part are separated from each other in the length direction when the diaper is spread open, the diaper is further provided with a leg sheet which has stretchability or elasticity, length direction circumferential edge regions of the leg sheet are respectively joined with substantially the entirety of a bottom edge region of the front part and substantially the entirety of a bottom edge region of the back part, whereby the leg sheet is arranged in the space between the front part and the back part, the diaper has depressed parts which extend from the two side edges inward when spread open, and the leg sheet which adjoins front-side starting ends of depressed parts or the front part and the leg sheet which adjoins back-side starting ends of depressed parts or the back part are joined with each other, whereby a pair of leg openings are defined.

According to a third aspect of the present invention, there is provided a disposable diaper which is provided with a single torso opening and a pair of leg openings, wherein the disposable diaper is provided with a front part and back part and with a crotch part, the front part and back part are separated from each other in the length direction when the diaper is spread open, the crotch part extends in the length direction at an intermediate position in the traverse direction, the front part and back part are joined, the diaper is further provided with a pair of leg sheets which have stretchability or elasticity, length direction circumferential edge regions and an inward side edge region of one leg sheet are respectively joined at one side of the crotch part with the bottom edge region of the front part and the bottom edge region of the back part and with the side edge region of the crotch part, whereby that one leg sheet is arranged at one side of the crotch part at the space between the front part and back part, length direction circumferential edge regions and an inward side edge region of the other leg sheet are respectively joined at the other side of the crotch part with the bottom edge region of the front part and the bottom edge region of the back part and with the side edge region of the crotch part, whereby that other leg sheet is arranged at the other side of the crotch part at the space between the front part and back part, an outward side edge region inside a front-side length direction circumferential edge region of one leg sheet or an outward side edge region of one leg sheet which adjoins this or a side edge region of the front part and an outward side edge region inside a back-side length direction circumferential edge region of one leg sheet or an outward side edge region of one leg sheet which adjoins this or a side edge region of the back part are joined, an outward side edge region inside a front-side length direction circumferential edge region of the other leg sheet or an outward side edge region of the other leg sheet which adjoins this or a side edge region of the front part and an outward side edge region inside a back-side length direction circumferential edge region of the other leg sheet or an outward side edge region of the leg sheet which adjoins this or a side edge region of the back part are joined, and intermediate regions between the mutually joined side edge regions are left unjoined, whereby a pair of leg openings are defined.

Advantageous Effects of Invention

It is possible to promote continued wearing of a diaper by a wearer.

BRIEF DESCRIPTION OF DRAWINGS

FIG. 4 is a schematic view which shows a method of production of a diaper of the first embodiment according to the present invention.

DESCRIPTION OF EMBODIMENTS

Figure 1:
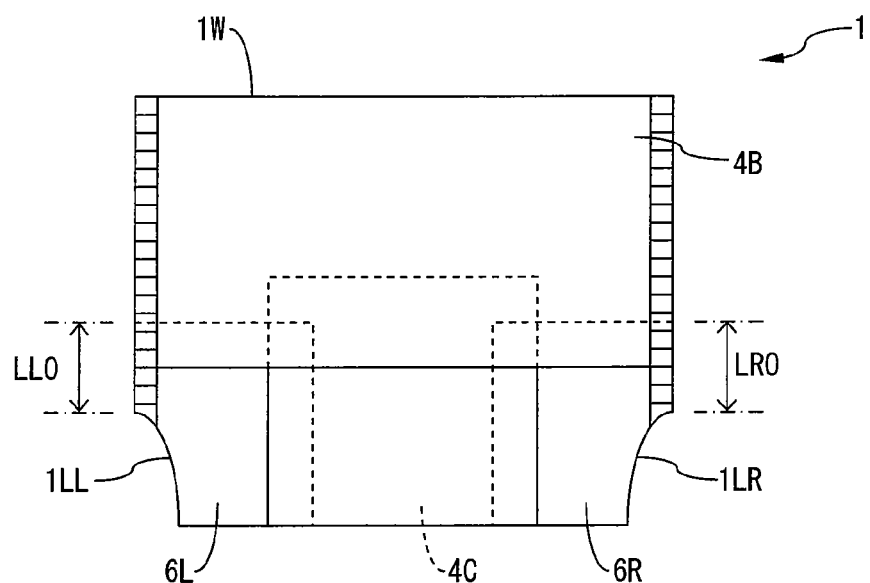
FIG. 1 is a plan view of a disposable diaper of a first embodiment according to the present invention.
Figure 2:
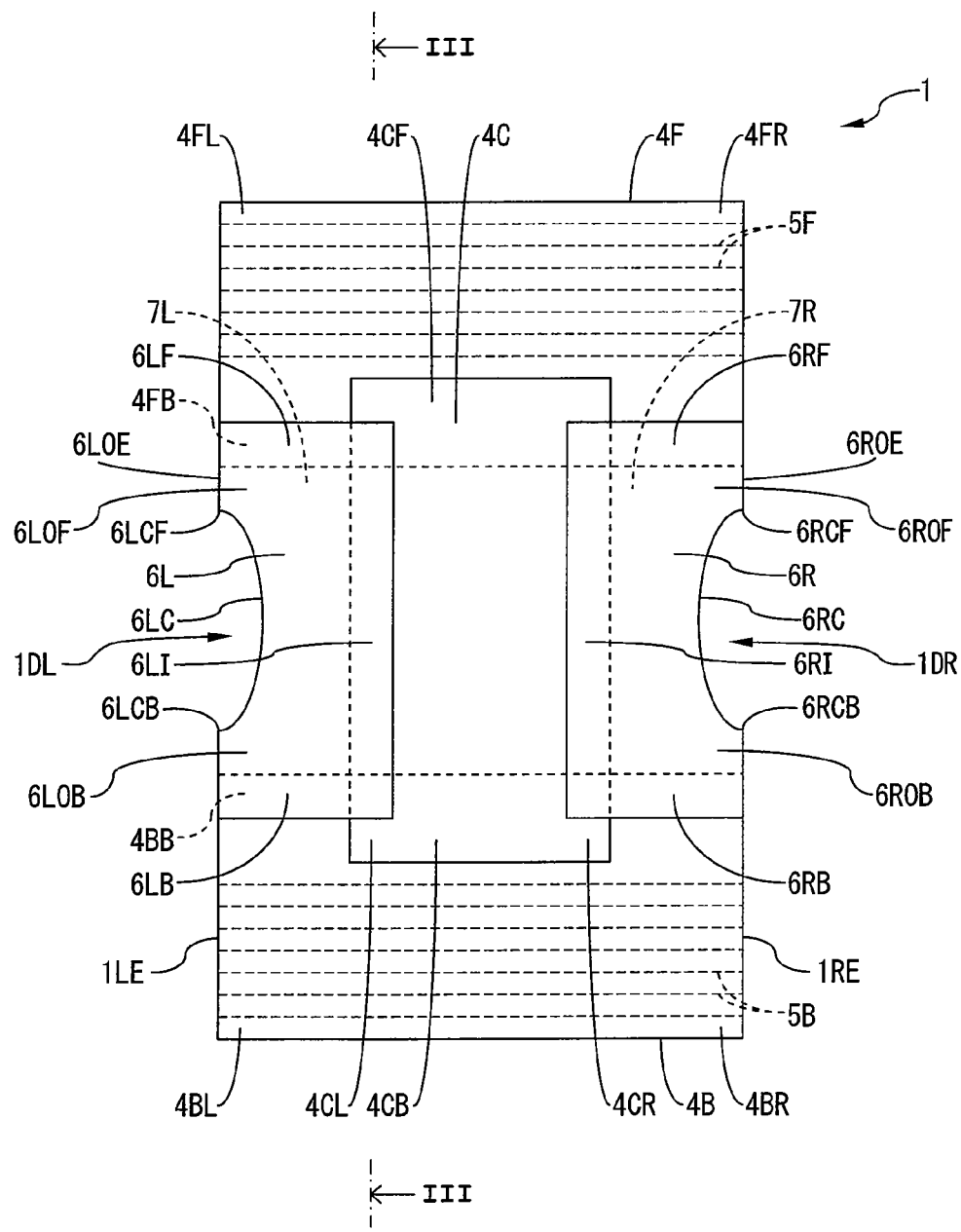
FIG. 2 is a spread open view of the diaper of FIG. 1.
Figure 3:
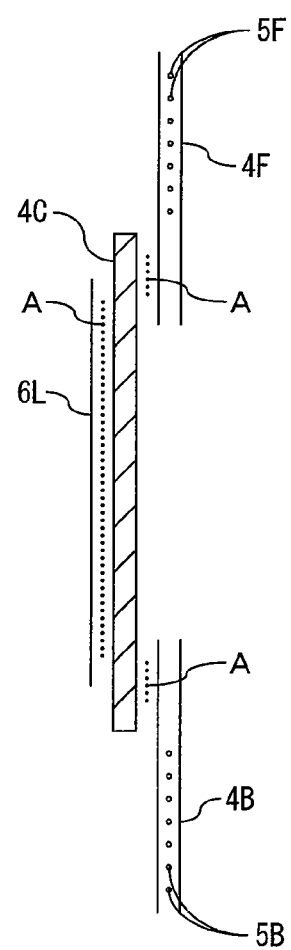
FIG. 3 is a cross-sectional view seen along the line III-III of FIG. 2.

FIG. 1, FIG. 2, and FIG. 3 show a first embodiment according to the present invention. Note that, in FIG. 2, L indicates a length direction of a diaper 1, while T indicates a traverse direction which perpendicularly intersects the length direction.

Referring to FIG. 1, FIG. 2, and FIG. 3, the disposable diaper 1 is provided with a front part 4F, a back part 4B, and a crotch part 4C. The front part 4F and the back part 4B are respectively positioned at the front side and the back side of the wearer when the diaper is worn.

The front part 4F and the back part 4B respectively form rectangular shapes and are arranged separated from each other in the length direction L when spread open. Further, at the front part 4F and the back part 4B, pluralities of elastic members 5F and 5B which extend substantially in parallel in the traverse direction T are provided. In particular, as shown in FIG. 3, the front part 4F and the back part 4B are provided with two liquid impermeable sheets which are superposed on each other. The elastic members 5F and 5B are arranged between these sheets in a stretched state and fastened to these sheets.

The crotch part 4C also forms a rectangular shape. It extends in the length direction L and is joined with the front part 4F and back part 4B at an intermediate position in the traverse direction. In this case, the length direction circumferential edge regions 4CF and 4CB of the crotch part 4C are joined to the bottom edge regions 4FB and 4BB of the front part 4F and back part 4B. As a result, the crotch part 4C is positioned at the crotch of the wearer when the diaper is worn.

This crotch part 4C is, for example, provided with a liquid impermeable back sheet and an absorbent member which is held at the back sheet. The absorbent member is for example provided with a fiber assembly and highly absorbent polymer particles.

The diaper 1 is further provided with a pair of substantially rectangular shape leg sheets 6L and 6R, that is, is provided with a left leg sheet 6L which is positioned at a left side of the crotch part 4C in FIG. 1 and FIG. 2 and a right leg sheet 6R which is positioned at a right side of the crotch part 4C. The leg sheets 6L and 6R have stretchability or elasticity and preferably have elasticity.

The elongation of the leg sheets 6L and 6R is preferably 140% or more, more preferably 180% or more. Here, the elongation of a sheet material is found as follows. That is, a 50 mm line segment is drawn on a sheet material in the natural state, then the sheet material is pulled to stretch it and the length B (mm) of the line when the material is completely stretched is measured. Next, the following formula is used to calculate the elongation:

$$\text{Elongation} = B/50 \times 100 (\%)$$

Furthermore, the leg sheet 6L and 6R have at least one of liquid impermeability, water repellency, and air permeability.

The leg sheets can be comprised from stretchable sheets or elastic sheets. As stretchable sheets, for example, polyethylene, polypropylene, or other thermoplastic resin films can be used. Alternatively, they may be comprised from composite sheets of thermoplastic resin films on which partially cut or weakened nonstretchable nonwoven fabrics are laminated. On the other hand, as the elastic sheets, for example, sheets which are made from nonwoven fabrics comprised of melted elastic fibers of urethane, styrene, or other such thermoplastic elastomer resin and composite sheets of nonwoven fabrics comprised of elastic fibers on which partially cut or weakened nonstretchable nonwoven fabrics are laminated.

The length direction circumferential edge regions 6LF and 6LB of the left leg sheet 6L are joined to the bottom edge region 4FB of the front part 4F and the bottom edge region 4BB of the back part 4B at the left of the crotch part 4C.

Further, the inward side edge region 6LI of the left leg sheet 6L is joined to the left side edge region 4CL of the crotch part 4C. As a result, the left leg sheet 6L is arranged at the space 7L between the front part 4F and back part 4B at the left of the crotch part 4C.

Similarly, the length direction circumferential edge regions 6RF and 6RB of the right leg sheet 6R are joined to the bottom edge region 4FB of the front part 4F and the bottom edge region 4BB of the back part 4B at the right of the crotch part 4C. Further, the inward side edge region 6RI of the right leg sheet 6R is joined to the right side edge region 4CR of the crotch part 4C. As a result, the right leg sheet 6R is arranged at the space 7R between the front part 4F and back part 4B at the right of the crotch part 4C.

Here, the front part 4F, back part 4B, crotch part 4C, left leg sheet 6L, and right leg sheet 6R are for example joined with each other by a hot melt adhesive A (FIG. 3).

In particular, as shown in FIG. 2, the diaper 1, when spread open, has depressed parts 1DL and 1DR which extend inward from the two side edges 1LE and 1RE. In the first embodiment according to the present invention, the left leg sheet 6L has a cutaway part 6LC which extends inward from the outward side edge 6LOE, while the right leg sheet 6R has a cutaway part 6RC which extends inward from the outward side edge 6ROE. The above-mentioned depressed parts 1DL, 1DR are defined by these cutaway parts 6LC and 6RC. Note that, in the first embodiment according to the present invention, the cutaway parts 6LC and 6RC respectively form semi-oval shapes which have long axes extending in the length direction.

On top of this, the outward side edge region 6LOF of the left leg sheet 6L adjoining the front-side starting end 6LCF of the depressed part 1DL or cutaway part 6LC and the outward side edge region 6LOB of the left leg sheet 6L adjoining the back-side starting end 6LCB of the depressed part 1DR or cutaway part 6LC are joined with each other. Further, the left side edge region 4FL of the front part 4F and the left side edge region 4BL of the back part 4B are joined with each other.

In the same way, the outward side edge region 6ROF of the right leg sheet 6R adjoining the front-side starting end 6RCF of the cutaway part 6RC and the outward side edge region 6ROB of the right leg sheet 6R adjoining the back-side starting end 6RCB of the cutaway part 6RC are joined with each other. Further, the right side edge region 4FR of the front part 4F and the right side edge region 4BR of the back part 4B are joined with each other.

As a result, as shown in FIG. 1, the left leg sheet 6L defines the left leg opening 1LL, while the right leg sheet 6R defines the right leg opening 1LR. Further, the front part 4F and back part 4B define a single leg opening 1W.

Here, the outward side edge regions 6LOF and 6LOB of the left leg sheet 6L, the outward side edge regions 6ROF and 6ROB of the right leg sheet 6R, and the left side edge regions 4FL and 4BL and right side edge regions 4FR and 4BR of the front part 4F and back part 4B are respectively, for example, joined by sonic seals and therefore are joined to be unable to be again joined. As a result, the diaper 1 forms a pants shape.

In the first embodiment according to the present invention, the cutaway parts 6LC and 6RC or depressed parts 1DL and 1DR are formed so that the circumferential lengths or inside diameters of the leg openings 1LL and 1LR become smaller than the circumferential lengths or inside diameters of the legs of the wearer.

When worn, the legs of the wearer are passed through the leg openings 1LL and 1LR then the diaper 1 is pulled up. In this case, the leg sheets 6L and 6R stretch in accordance with the shapes of the legs of the wearer. Therefore, the leg sheets 6L and 6R closely fit against the wearer.

Furthermore, the left leg sheet 6L and the right leg sheet 6R form ring shapes, so the leg sheets 6L and 6R can continue to closely fit against the entire circumferences of the legs of the wearer. As a result, leakage from the pair of leg openings 1LL and 1LR can be reliably suppressed. Further, separation of the leg sheets 6L and 6R from the front part 4F and back part 4B can be suppressed.

Here, the length direction length LLO of the outward side edge regions 6LOF and 6LOB of the left leg sheet 6L (FIG. 1) and the length direction length LRO of the outward side edge regions 6ROF and 6ROB of the right leg sheet 6R (FIG. 1) are respectively preferably 5 mm or more.

The leg sheets 6L and 6R preferably have stretchability or elasticity in two directions perpendicularly intersecting each other, for example, preferably have stretchability or elasticity in the length direction L and the traverse direction T. The leg sheets 6L and 6R may also have stretchability or elasticity in only one direction. When the cutaway parts 6LC and 6RC are semi-oval shapes which extend in the length direction, the leg sheets 6L and 6R preferably have stretchability or elasticity in the length direction L.

Furthermore, in the first embodiment according to the present invention, the skin-side surfaces of the leg sheets 6L and 6R are smooth. That is, the skin-side surfaces of the leg sheets 6L and 6R are not provided with wrinkles. As a result, the leg sheets 6L and 6R contact the wearer in the form of not line contact, but surface contact, so the contact of the leg sheets 6L and 6R with the wearer is improved.

Note that, by breaking the joined parts of the outward side edge regions 6LOF and 6LOB of the left leg sheet 6L or the joined parts of the outward side edge regions 6ROF and 6ROB of the right leg sheet 6R, it is possible to adjust the sizes of the leg openings 1LL and 1LR. In this case, the joining strength of the joined parts is preferably 6N/25 mm to 40N/25 mm, more preferably 8N/25 mm to 30N/25 mm. This is to enable the sizes of the leg openings 1LL and 1LR to be adjusted by breaking the joined parts while enabling prevention of unintentional breakage of the joined parts at the time of use of the diaper 1.

FIG. 4 schematically shows the method of production of the diaper 1 of the first embodiment according to the present invention. Note that, in FIG. 4, MD indicates the machine direction, while CD shows the crossing direction which perpendicularly intersects the machine direction MD.

Referring to FIG. 4, at step S11, the web W4F of the front part 4F and the web W4B of the back part 4B are conveyed in the machine direction MD while being separated from each other in the crossing direction CD. At the next step S12, the crotch parts 4C are superposed on and joined to the front part web W4F and the back part web W4B while separated in the machine direction MD. At the next step S13, leg sheet materials M6 which later form the leg sheets 6L and 6R are superposed on and joined to the front part web W4F, back part web W4B, and mutually adjoining pairs of crotch parts 4C. At the next step S14, through holes LH which later form the cutaway parts 6LC and 6RC are formed in the leg sheet materials M6.

At the next step S15, the crotch parts 4C and leg sheet materials M6 are folded along a folding line FL substantially parallel to the machine direction MD whereby the front part web W4F and back part web W4B are superposed against each other. At the next step S16, the front part web W4F and back part web W4B are joined with each other between the mutually adjoining pairs of the crotch part 4C and the parts of the mutually facing leg sheet materials M6 are joined with each other whereby joined parts J are formed separated in the machine direction MD. At the next step S17, the assemblies are cut along a cutting line CL running through the joined parts J. As a result, mutually separated diapers 1 are formed.

Note that, at step S12, back sheets which form the crotch parts 4C may be joined to the front part web W4F and back part web W4B, then the absorbent members which form the crotch part 4C joined to the back sheets.

Further, at step S13, the leg sheet materials M6 may be joined with the crotch parts 4C etc. in the stretched state or conversely may be joined without stretching them.

Further, at step S14, leg sheet materials M6 in which through holes LH are formed may be superposed on and joined with the front part web W4F, the back part web W4B, and the crotch parts 4C.

Figure 5A:
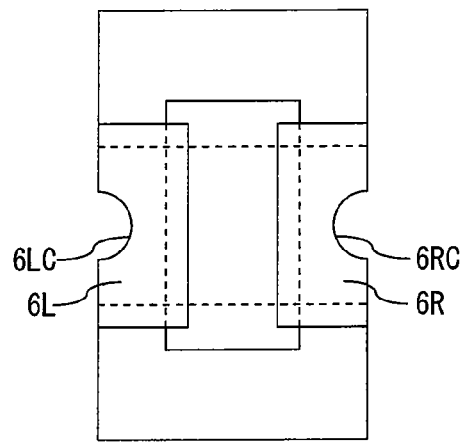
FIG. 5A is a view which shows another embodiment of cutaway parts.
Figure 5B:
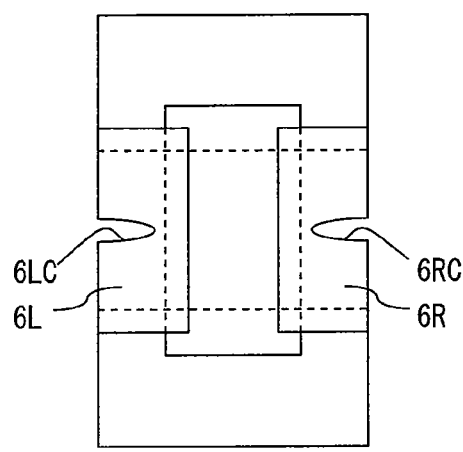
FIG. 5B is a view which shows another embodiment of cutaway parts.
Figure 5C:
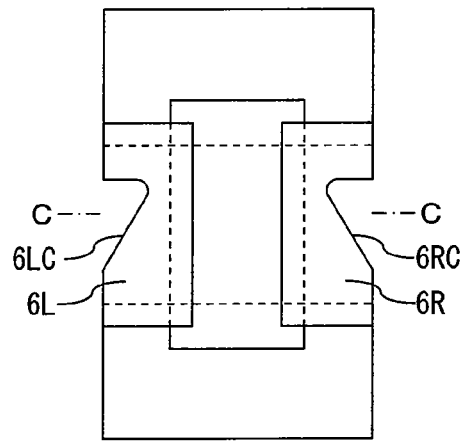
FIG. 5C is a view which shows another embodiment of cutaway parts.
Figure 5D:
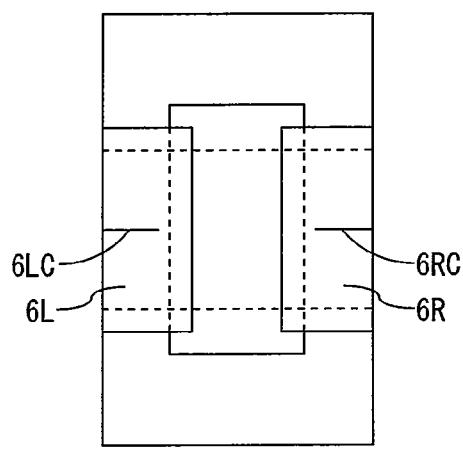
FIG. 5D is a view which shows another embodiment of cutaway parts.

FIG. 5A, FIG. 5B, FIG. 5C, and FIG. 5D show other embodiments of the cutaway parts 6LC and 6RC. The cutaway parts 6LC and 6RC respectively form semi-circular shapes in the example which is shown in FIG. 5A, semi-oval shapes which have long axes extending in the traverse direction in the example which is shown in FIG. 5B, and asymmetric shapes with respect to the length direction center line C-C in the example which is shown in FIG. 5C. Further, in the example which is shown in FIG. 5D, the cutaway parts 6LC and 6RC are respectively comprised of slits.

Note that, in the examples which are shown in FIG. 5B and FIG. 5D, the leg sheets 6L and 6R preferably have stretchability or elasticity in at least the traverse direction T.

When the cutaway parts 6LC and 6RC are long in the length direction as shown in FIG. 2, the leg openings 1LL and 1LR can be positioned at the groin part of the wearer. In this case, the worn appearance of the wearer can be streamlined.

On the other hand, when the cutaway parts 6LC and 6RC are long in the traverse direction such as shown in FIG. 5B and FIG. 5D, the leg openings 1LL and 1LR can be positioned at the thigh parts of the wearer. In this case, the moving parts of the wearer can be kept from being tightened and the diaper 1 can be used to cover the body of the wearer over a wide range.

Whatever the case, the leg openings 1LL and 1LR are formed smaller than the legs of the wearer, so when the diaper is worn, the leg sheets 6L and 6R can be reliably closely fit with the legs of the wearer.

In the above-mentioned first embodiment according to the present invention, the outward side edge regions 6LOF and GLOB of the left leg sheet 6L and the outward side edge regions 6ROF and 6ROB of the right leg sheet 6R are respectively joined in a manner unable to be rejoined. However, these outward side edge regions 6LOF and 6LOB and outward side edge regions 6ROF and 6ROB can respectively be joined in a manner able to be rejoined by using for example fasteners.

Figure 6A:
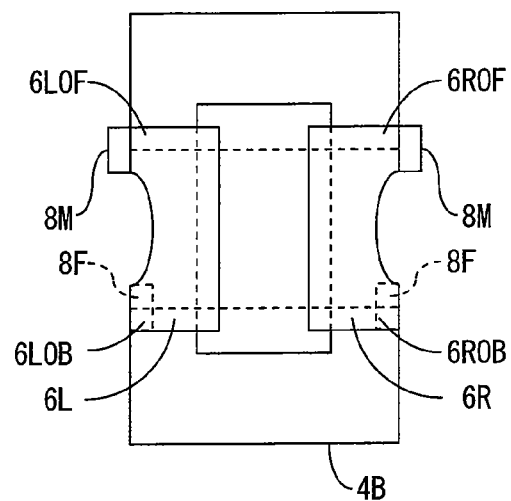
FIG. 6A is a view which shows another embodiment of joining.

That is, in the example which is shown in FIG. 6A, fasteners such as fasteners including male members 8M and female members 8F are provided. The male members 8M are provided adjoining the outward side edge regions 6LOF and 6ROF while projecting outward, while the female members 8F are provided at the outer surfaces of the back part 4B so as to overlap the outward side edge regions 6LOB and 6ROB.

Figure 6B:
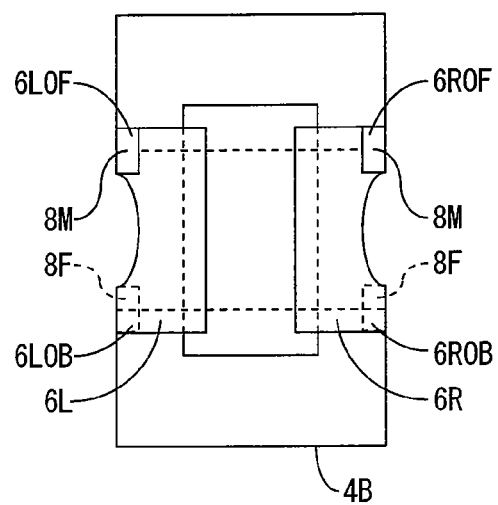
FIG. 6B is a view which shows another embodiment of joining.

On the other hand, in the example which is shown in FIG. 6B, the male members 8M are provided at the inner surfaces of the leg sheets 6L and 6R so as to overlap the outward side edge regions 6LOF and 6ROF. The female members 8F are similar to those in the example of FIG. 6A.

In the examples which are shown in FIG. 6A and FIG. 6B as well, the extents of overlap of the male members 8M and female members 8F can be changed so as to adjust the sizes of the leg openings 1LL and 1LR.

Figure 7A:
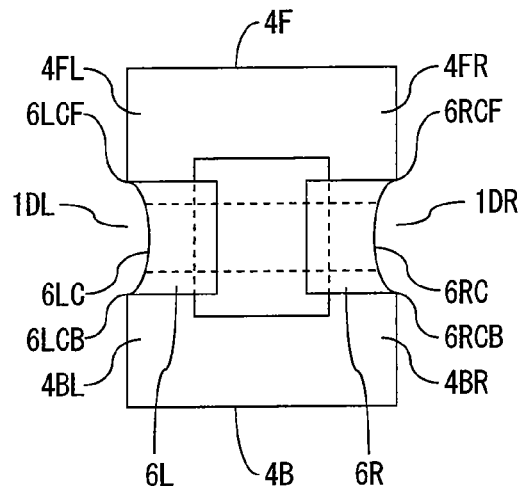
FIG. 7A is a view which shows another embodiment of depressed parts.
Figure 7B:
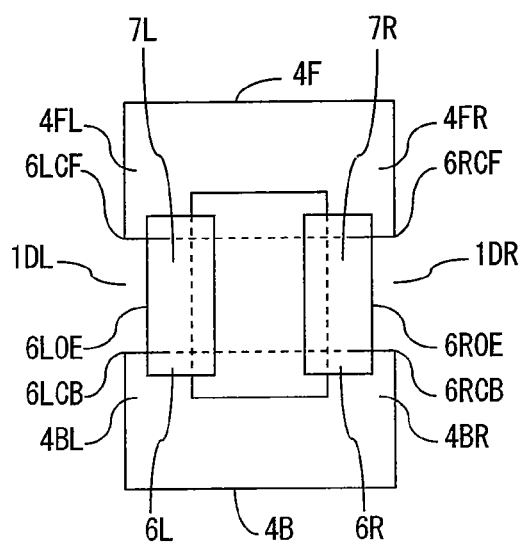
FIG. 7B is a view which shows another embodiment of depressed parts.

FIG. 7A and FIG. 7B show other embodiments of the depressed parts 1DL and 1DR. In the embodiments which were explained up to here, the cutaway part 6LC was formed in the left leg sheet 6L so that the outward side edge regions 6LOF and 6LOB were formed, while the cutaway part 6RC was formed in the right leg sheet 6R so that the outward side edge regions 6ROF and 6ROB were formed. As opposed to this, in the example which is shown in FIG. 7A, the cutaway parts 6LC and 6RC are formed so that the outward side edge regions are not formed, while these cutaway parts 6LC and 6RC define the depressed parts 1DL and 1DR.

In this case, the left side edge region 4FL of the front part 4F which adjoins the front-side starting end 6LCF of the cutaway parts 6LC and the left side edge region 4BL of the back part 4B which adjoins the back-side starting end 6LCB of the cutaway parts 6LC are joined together. Further, the right side edge region 4RL of the front part 4F which adjoins the front-side starting end 6RCF of the cutaway part 6RC and the right side edge region 4BR of the back part 4B which adjoins the back-side starting end 6RCB of the cutaway part 6RC are joined together.

In the example which is shown in FIG. 7B, the leg sheets 6L and 6R do not have cutaway parts. However, the traverse direction lengths of the leg sheets 6L and 6R are shorter than the traverse direction lengths of the spaces 7L and 7R. Therefore, the depressed part 1DL is defined by the outward side edge 6LOE of the leg sheet 6L, the bottom edge of the front part 4F, and the bottom edge of the back part 4B. In this case, the left side edge region 4FL of the front part 4F which adjoins the front-side starting end 6LCF of the depressed part 1DL and the left side edge region 4BL of the back part 4B which adjoins the back-side starting end 6LCB of the depressed part 1DL are joined with each other. Further, the right side edge region 4RL of the front part 4F which adjoins the front-side starting end 6RCF of the depressed part 1DR and the right side edge region 4BR of the back part 4B which adjoins the back-side starting end 6RCB of the depressed part 1DR are joined with each other.

Figure 8A:
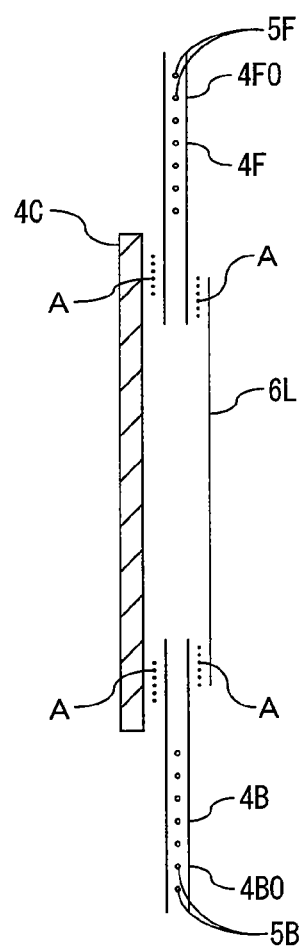
FIG. 8A is a view which shows another embodiment of a leg sheet.
Figure 8B:
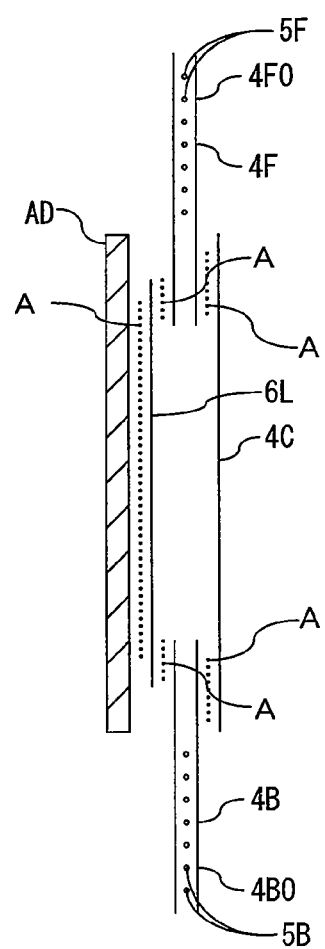
FIG. 8B is a view which shows another embodiment of a crotch part.
Figure 8C:
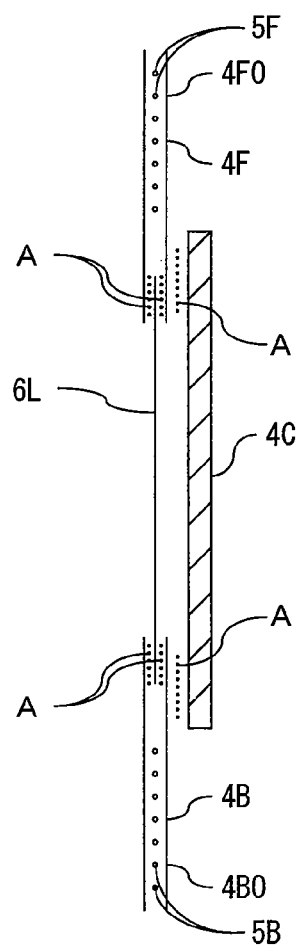
FIG. 8C is a view which shows another embodiment of a crotch part.

FIG. 8A shows another embodiment of the leg sheets 6L and 6R, while FIG. 8B and FIG. 8C shows other embodiments of the crotch part 4C. In the embodiments which were explained up to here, the leg sheets 6L and 6R were joined to the inside surfaces of the front part 4F and back part 4B, that is, the wearer side. As opposed to this, in the example which is shown in FIG. 8A, the leg sheets 6L and 6R are joined to the outside surface 4FO of the front part 4F and the outside surface 4BO of the back part 4B.

In the example which is shown in FIG. 8B, the absorbent member AD is provided separate from the crotch part 4C. That is, the crotch part 4C is provided with a back sheet, but is not provided with an absorbent member. On top of this, the crotch part 4C is joined with the outside surface 4FO of the front part 4F and the outside surface 4BO of the back part 4B.

On the other hand, in the example which is shown in FIG. 8C, the crotch part 4C which is provided with the back sheet and absorbent member is joined with the outside surface 4FO of the front part 4FO and the outside surface 4BO of the back part 4B. Further, the leg sheets 6L and 6R are joined between the two sheets which form the front part 4F and between the two sheets which form the back part 4B.

Figure 9:
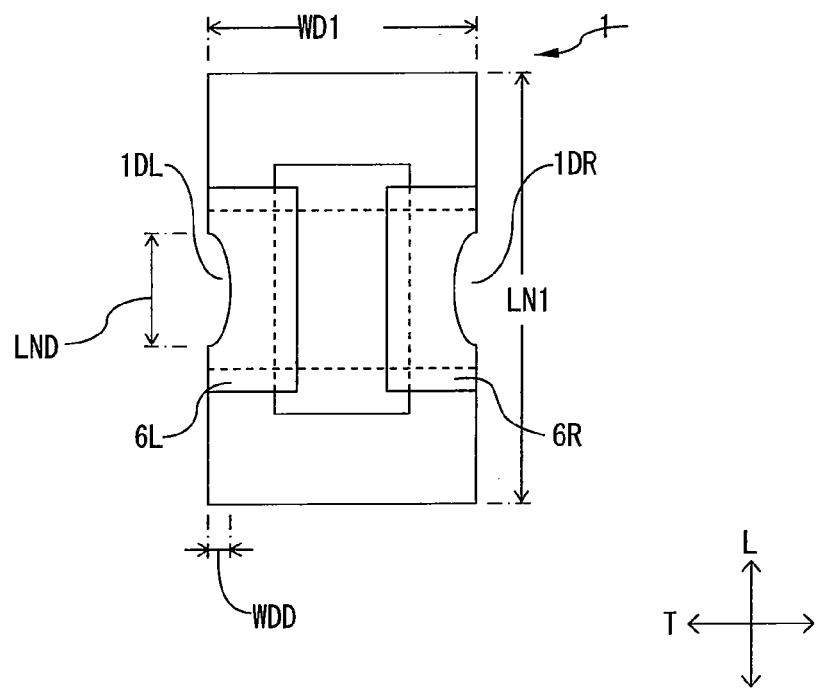
FIG. 9 is a view which explains dimensions of cutaway parts.

Next, the dimensions of the depressed parts 1DL and 1DR and the cutaway parts 6LC and 6RC will be explained while referring to FIG. 9. In the first embodiment according to the present invention, the depressed parts 1DL and 1DR are formed so that the length direction length LND of the depressed parts 1DL and 1DR is not more than ⅓ of the length direction length LN1 of the diaper 1 (LND≤(⅓)LN1) and so that the traverse direction length WDD of the depressed parts 1DL and 1DR is not more than ⅓ of the traverse direction length WD1 of the diaper 1 (WDD≤(⅓)WD1).

If formed in this way, the leg openings 1LL and 1LR can be made smaller in size while the body of the wearer can be sufficiently covered by the diaper 1. Therefore, the leg sheets 6L and 6R can be reliably fit against the legs of the wearer.

This was confirmed experimentally as well. That is, a plurality of diapers with different length direction lengths LN1 and traverse direction lengths WD1 such as child diapers and adult diapers, that is, LND≤(⅓)LN1 and WDD≤(⅓)WD1 diapers and LND>(⅓)LN1 or WDD>(⅓)WD1 diapers, were prepared. These diapers were checked for frequency of leakage. With the LND≤(⅓)LN1 and WDD≤(⅓)WD1 diapers, low frequencies of leakage were obtained. As opposed to this, with the LND>(⅓)LN1 or WDD>(⅓)WD1 diapers, high frequencies of leakage were obtained.

Figure 10:
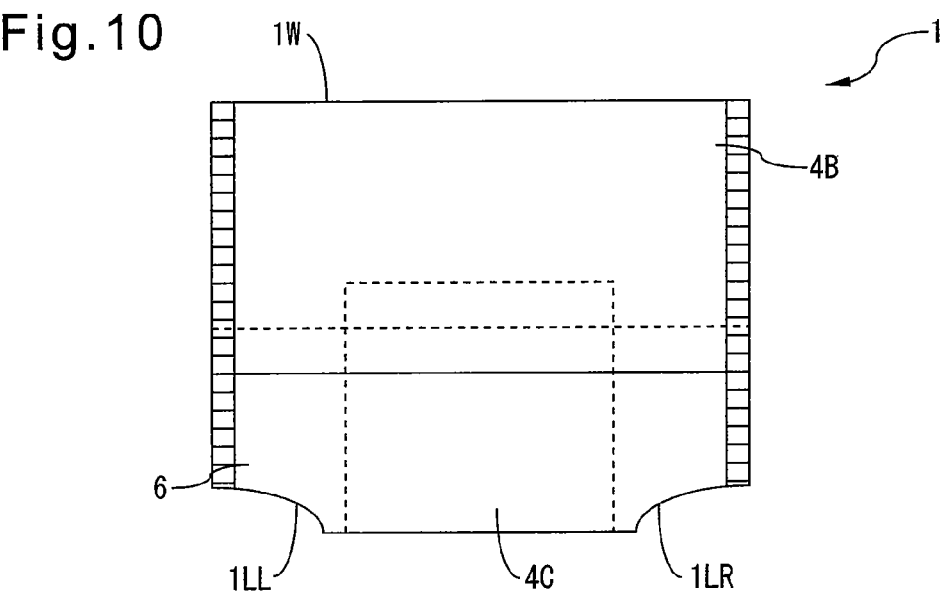
FIG. 10 is a plan view of a disposable diaper of a second embodiment according to the present invention.
Figure 11:
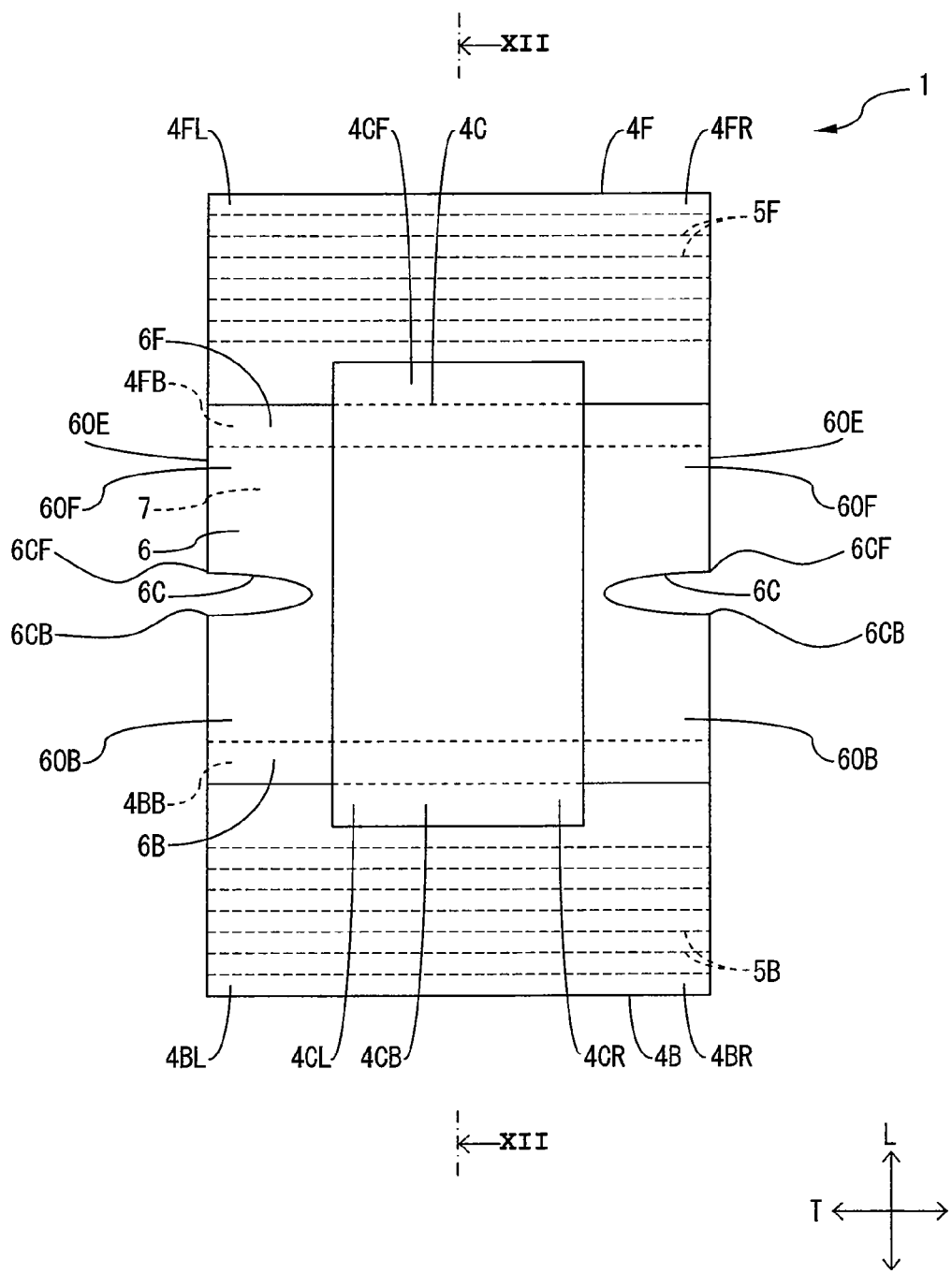
FIG. 11 is a spread open view of the diaper of FIG. 10.
Figure 12:
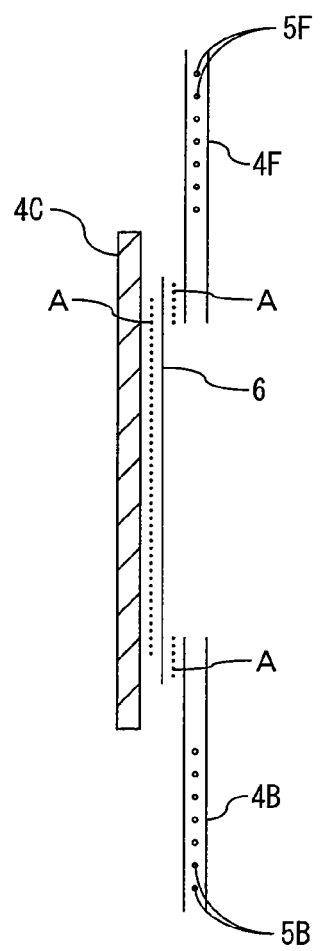
FIG. 12 is a cross-sectional view seen along the line XII-XII of FIG. 11.

FIG. 10, FIG. 11, and FIG. 12 show a second embodiment according to the present invention. Referring to FIG. 10, FIG. 11, and FIG. 12, in the second embodiment, a single leg sheet 6 is provided. This leg sheet 6 has substantially the same traverse direction length as the front part 4F and back part 4B.

The length direction circumferential edge regions 6F and 6B of the leg sheet 6 are respectively joined to the substantial entirety of the bottom edge region 4FB of the front part 4F and the substantial entirety of the bottom edge region 4BB of the back part 4B. As a result, the leg sheet 6 is arranged in the space 7 between the front part 4F and the back part 4B.

In particular, as shown in FIG. 11, the leg sheet 6 has a pair of cutaway parts 6C which extend from the side edges 60E inward. In the second embodiment according to the present invention, the cutaway parts 6C form semi-oval shapes which have long axes extending in the traverse direction.

On top of this, the side edge region 60F of the leg sheet 6 which adjoins the front-side starting ends 6CF of the cutaway parts 6C and the side edge region 60B of the leg sheet 6 which adjoins the back-side starting ends 6CB of the cutaway parts 6C are joined together.

As a result, as shown in FIG. 10, the leg sheet 6 defines a pair of leg openings 1LL and 1LR.

Figure 13:
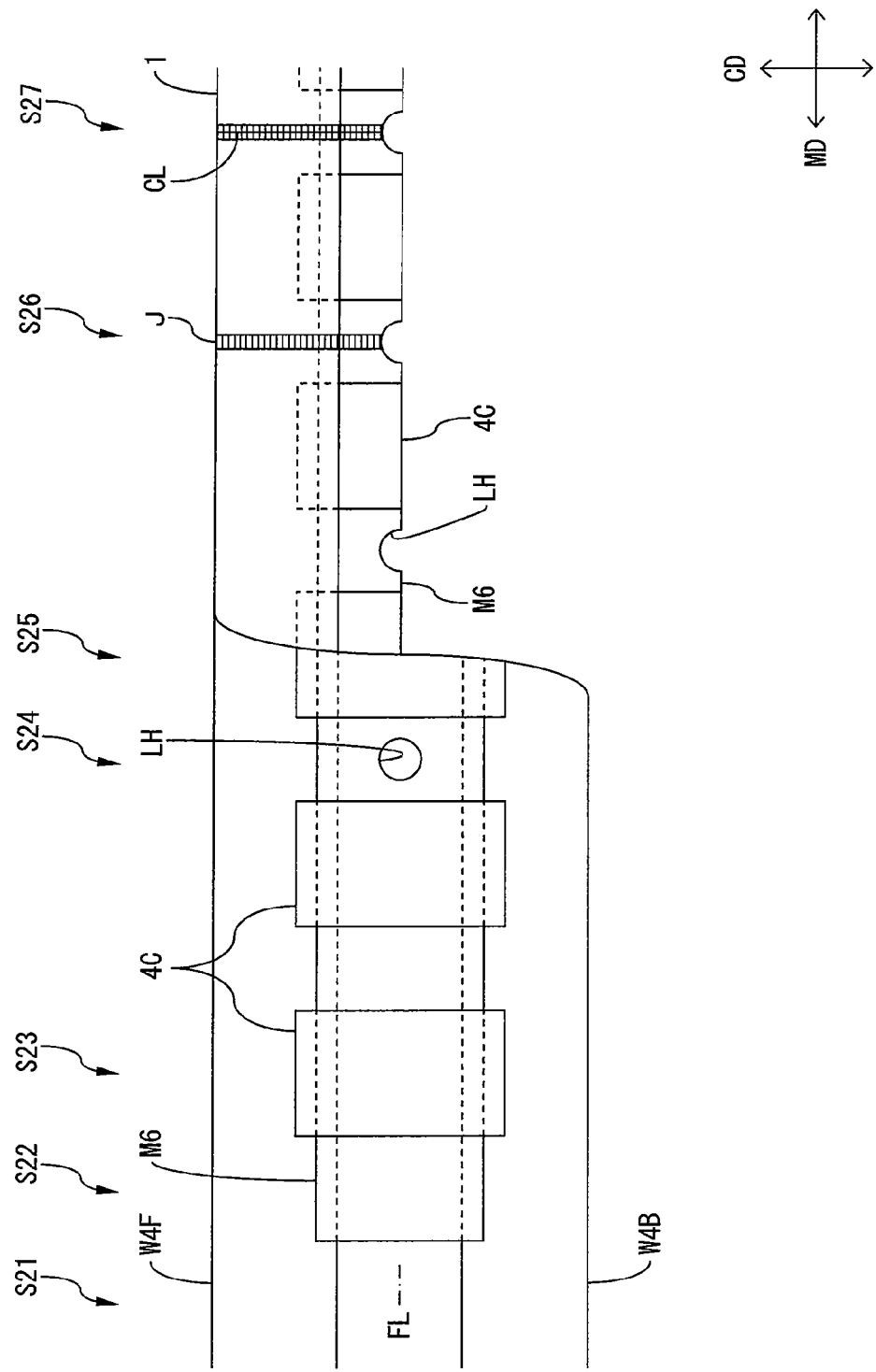
FIG. 13 is a schematic view which shows a method of production of a diaper of the second embodiment according to the present invention.

FIG. 13 schematically shows a method of production of a diaper 1 of a second embodiment according to the present invention. Note that, in FIG. 13, MD indicates a machine direction, while CD indicates a crossing direction which perpendicularly intersects the machine direction MD.

Referring to FIG. 13, at step S21, the web W4F of the front part 4F and the web W4B of the back part 4B are conveyed in the machine direction MD while being separated from each other in the crossing direction CD. At the next step S22, leg sheet materials M6 which later form the leg sheets 6L and 6R are superposed on and joined to the front part web W4F and back part web W4B. At the next step S23, the crotch parts 4C are superposed on and joined to the front part web W4F, the back part web W4B, and the leg sheet materials M6 while separated in the machine direction MD. At the next step S24, through holes LH which later form the cutaway parts 6LC and 6RC are formed in the leg sheet materials M6.

At the next step S25, the crotch parts 4C and leg sheet materials M6 are folded along a folding line FL substantially parallel to the machine direction MD whereby the front part web W4F and back part web W4B are superposed against each other. At the next step S26, joined parts J are formed separated in the machine direction MD between the mutually adjoining pair of crotch parts 4C. At the next step S27, the assemblies are cut along a cutting line CL running through the joined parts J. As a result, mutually separated diapers 1 are formed.

Note that, regarding steps S22 and S23, it is also possible to join the crotch parts 4C to the leg sheet materials M6 in advance and then superpose them on the front part web W4F and back part web W4B.

In the second embodiment according to the present invention, the crotch part 4C is joined to both the front part 4F and back part 4B. However, the crotch part 4C may also be joined to one of the front part 4F and back part 4B or may be not joined to either of them.

The rest of the configuration and actions of the second embodiment according to the present invention are similar to the configuration and actions of the first embodiment.

Figure 14:
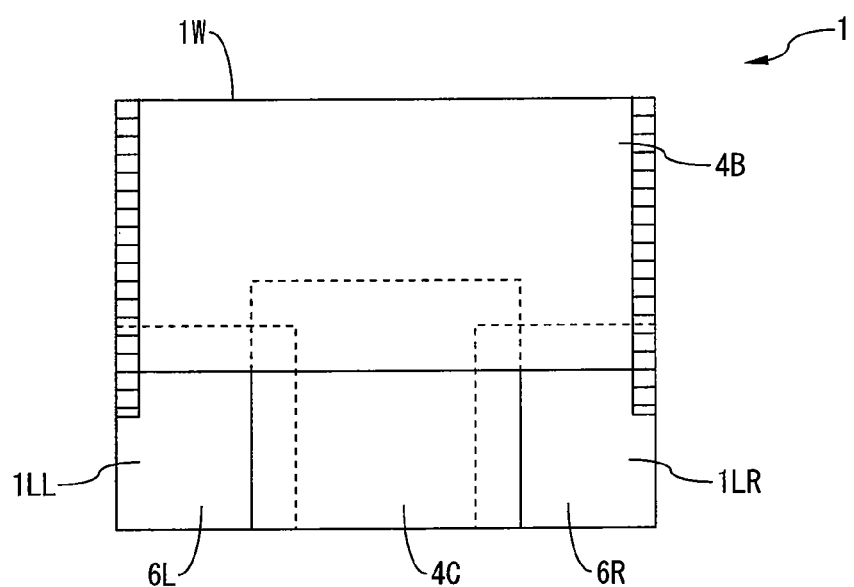
FIG. 14 is a plan view of a disposable diaper of a third embodiment according to the present invention.
Figure 15:
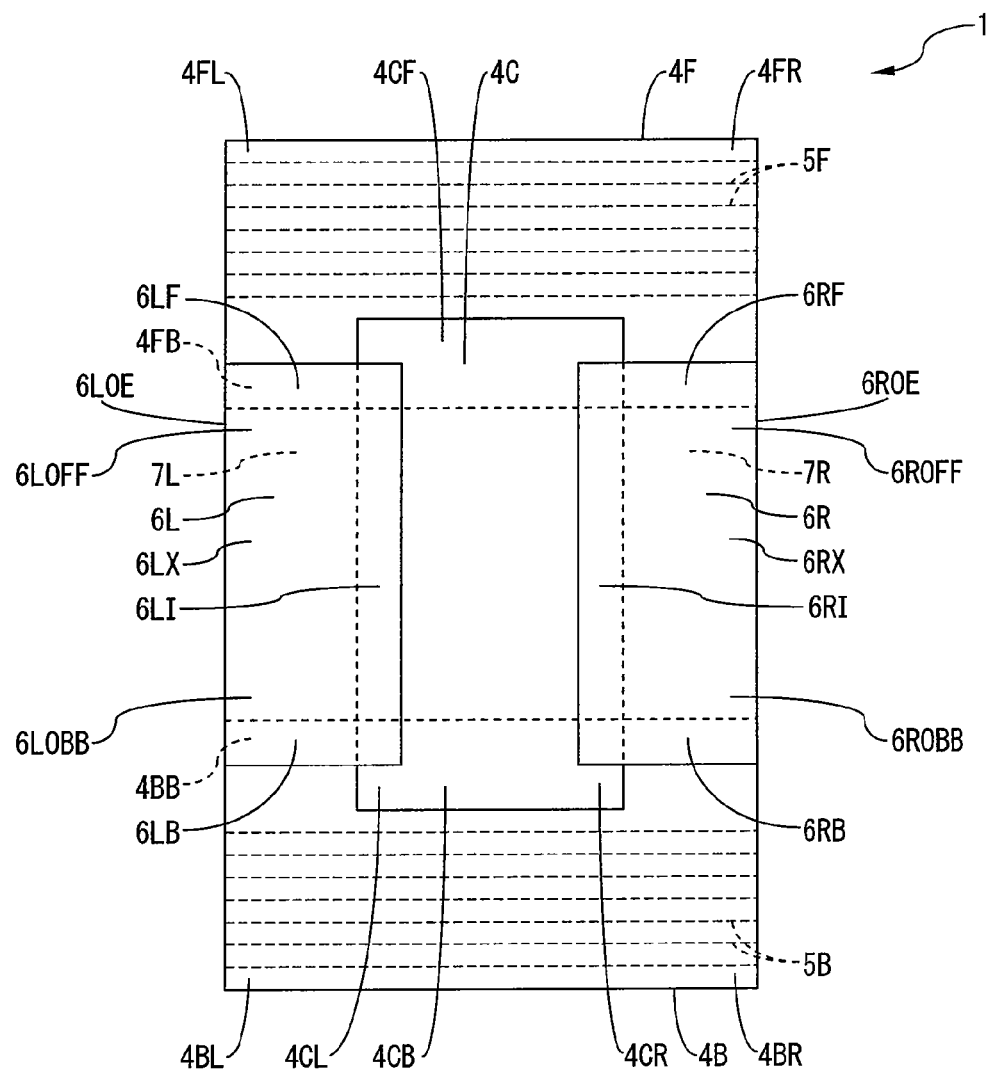
FIG. 15 is a spread open view of the diaper of FIG. 14.

FIG. 14 and FIG. 15 show a third embodiment according to the present invention. If referring to FIG. 14 and FIG. 15, in the third embodiment according to the present invention, in the same way as the first embodiment, a left leg sheet 6L and right leg sheet 6R are provided. However, the left leg sheet 6L and the right leg sheet 6R are not provided with cutaway parts. Therefore, the two side edges of the diaper 1 are not provided with depressed parts.

On top of this, the inside of the front-side length direction circumferential edge region 6LF of the left leg sheet 6L or the outward side edge region 6LOFF of the left leg sheet 6L adjoining this and the inside of the back-side length direction circumferential edge region 6LB of the left leg sheet 6L or the outward side edge region 6LOBB of the left leg sheet 6L adjoining it are joined with each other. At this time, the intermediate region 6LX between the mutually joined outward side edge regions 6LOFF and 6LOBB remains without being joined. The left leg opening 1LL is defined in this way.

Similarly, the inside of the front-side length direction circumferential edge region 6RF of the right leg sheet 6R or the outward side edge region 6ROFF of the right leg sheet 6R adjoining this and the inside of the back-side length direction circumferential edge region 6RB of the right leg sheet 6R or the outward side edge region 6ROBB of the right leg sheet 6R adjoining it are joined with each other. At this time, the intermediate region 6RX between the mutually joined outward side edge regions 6ROFF and 6ROBB remains without being joined. The right leg opening 1LR is defined in this way.

If doing this, there is no need to form cutaway parts and no trim occurs.

The left side edge region 4FL of the front part 4F which adjoins the front-side length direction circumferential edge region 6LF of the left leg sheet 6L and the left side edge region 4BL of the back part 4B which adjoins the back-side length direction circumferential edge region 6LB of the left leg sheet 6L may be joined with each other and the right side edge region 4FR of the front part 4F which adjoins the front-side length direction circumferential edge region 6RF of the right leg sheet 6R and the right side edge region 4BR of the back part 4B which adjoins the back-side length direction circumferential edge regions 6RB of the right leg sheet 6R may be joined with each other.

Note that the rest of the configuration and actions of the third embodiment according to the present invention are similar to the configuration and actions of the first embodiment.

Figure 16:
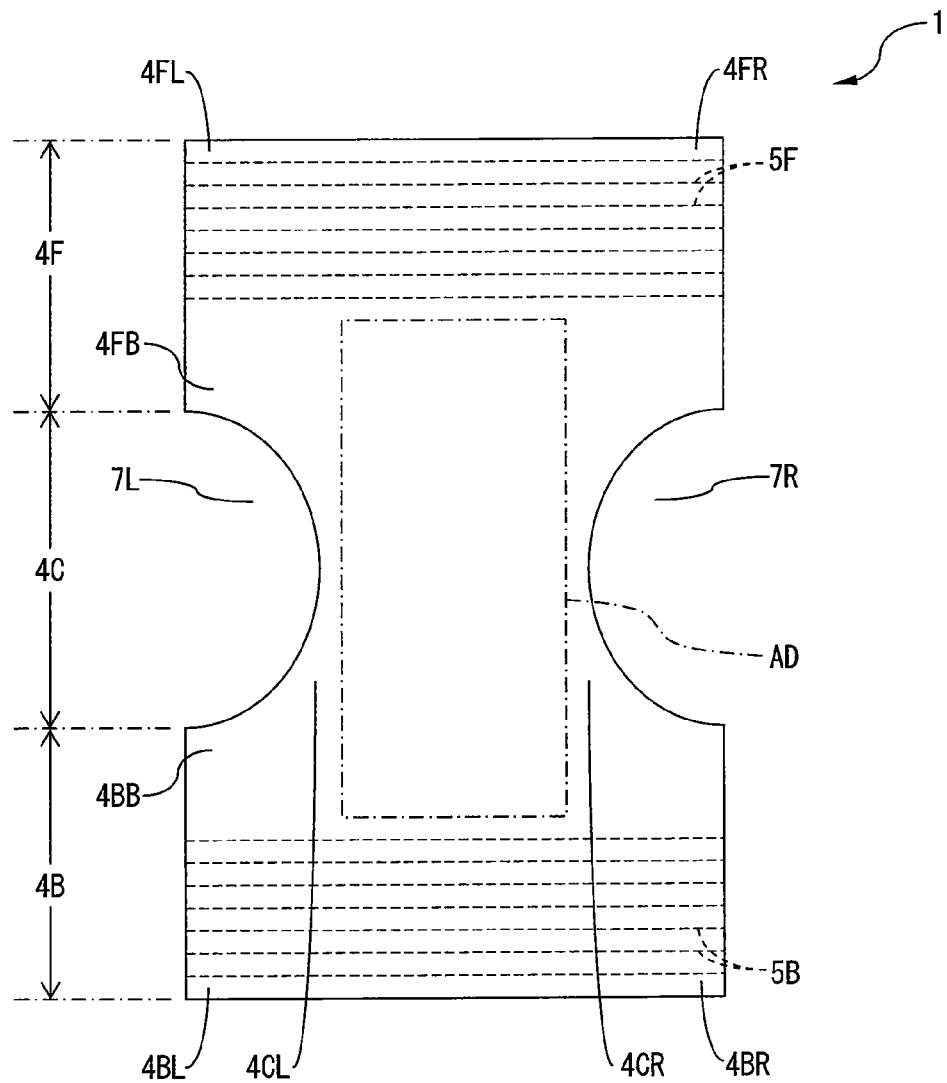
FIG. 16 is a view which shows still another embodiment of a disposable diaper.

In the embodiments which have been explained up to here, the front part 4F, back part 4B, and crotch part 4C are comprised from mutually separate members. However, as shown in FIG. 16, the front part 4F and back part 4B and the crotch part 4C which is comprised from the back sheet may also be comprised from a common sheet material and the absorbent member AD may be arranged on this sheet material. Note that, in FIG. 16, the leg sheets 6L and 6R are omitted.

Further, the two sides of the crotch part 4C or absorbent member in the traverse direction may also be provided with leak-proofing members. The leak-proofing members are, for example, provided with sheets which spread outward in the traverse direction from the traverse direction side edges of the absorbent member. Elastic members which extend in the length direction are provided at the outer ends of these sheets. As a result, leakage can be reliably suppressed.

Further, the embodiments which are explained up to here may be combined with each other. That is, for example, in the second and third embodiments, as shown in FIG. 8A, the leg sheets may also be joined to the outer surfaces of the front part 4F and back part 4B.

The present invention claims the benefit of Japanese Patent Application No. 2011-002161 the entire disclosure of which is cited here.

REFERENCE SIGNS LIST 1 disposable diaper
1LL, 1LR leg openings
4F front part
4B back part
4C crotch part
6L, 6R leg sheets
6LC, 6RC cutaway parts
6LOF, 6LOB, 6ROF, 6ROB outward side edge regions

The invention claimed is:

1. A disposable diaper which is provided with a single torso opening and a pair of leg openings, wherein
the disposable diaper is provided with a front part and back part and with a crotch part, the front part and back part each has a bottom edge region and said bottom edge regions and the front and back part are separated from each other in the length direction when the diaper is spread open, the crotch part has a length direction, circumferential edge regions and side edge regions and extends in the length direction at an intermediate position in the traverse direction,
said diaper is further provided with a pair of leg sheets which each have stretchability or elasticity and each have a length direction, circumferential edge regions, an inward side edge region, and an outward side edge region,
the length direction circumferential edge regions and inward side edge region of one leg sheet of the pair of leg sheets are respectively joined at one side of the crotch part with the bottom edge region of the front part and the bottom edge region of the back part and with one side edge region of the side edge regions of the crotch part, whereby said one leg sheet is arranged at one side of the crotch part at a space between the front part and back part,
the length direction circumferential edge regions and inward side edge region of an other leg sheet of the pair of leg sheets are respectively joined at an other side of the crotch part with the bottom edge region of the front part and the bottom edge region of the back part and with an other side edge region of the side edge regions of the crotch part, whereby the other leg sheet is arranged at the other side of the crotch part at the space between the front part and back part,
the diaper has depressed parts which extend from the outward side edges of the leg sheets inward when spread open,
outward side edges of the leg sheets adjacent to front-side starting ends of depressed parts and side edge regions of the front part are respectively joined with outward side edges of the leg sheets adjacent to back-side starting ends of depressed parts and side regions of the back part, whereby a pair of leg openings are defined,
the leg sheets have a smooth skin side surface that is non-wrinkled,
the depressed parts are respectively defined by cutaway parts, the cutaway parts respectively having a semi-oval shape having a long axis extending in the length direction, and
the outward side edge regions adjacent to front-side starting ends and the outward side edge regions adjacent to back-side starting ends respectively have a length direction length of 5 mm or more.

2. The disposable diaper as set forth in claim 1, wherein the outward side edges of the leg sheets adjacent to front-side starting ends of the depressed parts or the side edge regions of the front part are respectively joined to be unable to be rejoined with the outward side edges of the leg sheets adjacent to back-side starting ends of the depressed parts or the side edge regions of the back part.

3. The disposable diaper as set forth in claim 1, wherein side edge regions of the front part and back part are joined together to be unable to be rejoined whereby said diaper forms a pants shape.

4. The disposable diaper as set forth in claim 1, wherein the outward side edges of the leg sheets adjacent to front-side starting ends of the depressed parts and the side edge regions of the front part are respectively joined together with the outward side edges of the leg sheets adjacent to back-side starting ends of the depressed parts and the side edge regions of the back part to be able to be rejoined.

5. The disposable diaper as set forth in claim 1, wherein the leg sheets are formed so that the leg openings are positioned at the thigh parts of the wearer when the diaper is worn.

6. The disposable diaper as set forth in claim 1, wherein the leg sheets have stretchability or elasticity in two mutually perpendicular intersecting directions.

7. The disposable diaper as set forth in claim 1, wherein the leg openings are adjustable in size.

8. The disposable diaper as set forth in claim 1, wherein the leg sheets have liquid impermeability.

9. The disposable diaper as set forth in claim 1, wherein the leg sheets have water repellency.

10. The disposable diaper as set forth in claim 1, wherein the front part and back part are provided with pluralities of elastic members which extend substantially in parallel to the traverse direction.

* * * * *